(12) United States Patent
Lamego et al.

(10) Patent No.: US 9,622,692 B2
(45) Date of Patent: Apr. 18, 2017

(54) PERSONAL HEALTH DEVICE

(75) Inventors: Marcelo M. Lamego, Coto De Caza, CA (US); Massi Joe E. Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 636 days.

(21) Appl. No.: 13/473,477

(22) Filed: May 16, 2012

(65) Prior Publication Data

US 2012/0296178 A1 Nov. 22, 2012

Related U.S. Application Data

(60) Provisional application No. 61/486,689, filed on May 16, 2011.

(51) Int. Cl.
*A61B 5/1455* (2006.01)

(52) U.S. Cl.
CPC .................................. *A61B 5/1455* (2013.01)

(58) Field of Classification Search
CPC .............. A61B 5/1455; A61B 5/14551; A61B 5/14552; A61B 5/14532
USPC ....... 600/310, 316, 322, 323, 324, 326, 333, 600/334, 335, 336, 340, 344, 473, 476; 356/41
See application file for complete search history.

(56) References Cited

U.S. PATENT DOCUMENTS

| | | | |
|---|---|---|---|
| 4,308,871 A * | 1/1982 | Shouda et al. | 600/499 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |

(Continued)

OTHER PUBLICATIONS

US 8,845,543, 09/2014, Diab et al. (withdrawn)

*Primary Examiner* — Tse Chen
*Assistant Examiner* — Chu Chuan (JJ) Liu
(74) *Attorney, Agent, or Firm* — Knobbe, Martens, Olson & Bear, LLP

(57) ABSTRACT

An active pulse blood constituent monitor is disclosed. A sensor configured to provide an artificial excitation to a portion of the patient at a known frequency provides additional information in determining the physiological condition of the patient.

16 Claims, 13 Drawing Sheets

(56) References Cited

U.S. PATENT DOCUMENTS

| | | |
|---|---|---|
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |

(56) References Cited

U.S. PATENT DOCUMENTS

| | | |
|---|---|---|
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |

(56) References Cited

U.S. PATENT DOCUMENTS

| | | |
|---|---|---|
| 8,355,766 B2 | 1/2013 | Macneish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 2005/0256386 A1* | 11/2005 | Chan et al. .................. 600/323 |
| 2007/0043281 A1* | 2/2007 | Fine ..................... A61B 5/1455 600/335 |
| 2009/0030330 A1* | 1/2009 | Kiani .................. A61B 5/14551 600/500 |
| 2009/0247984 A1 | 10/2009 | Lamego et al. |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |

(56) References Cited

U.S. PATENT DOCUMENTS

| | | |
|---|---|---|
| 2011/0105854 A1 | 5/2011 | Kiani et al. |
| 2011/0208015 A1 | 8/2011 | Welch et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2012/0059267 A1 | 3/2012 | Lamego et al. |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | O'Neil et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |
| 2014/0025306 A1 | 1/2014 | Weber et al. |
| 2014/0034353 A1 | 2/2014 | AL-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

\* cited by examiner

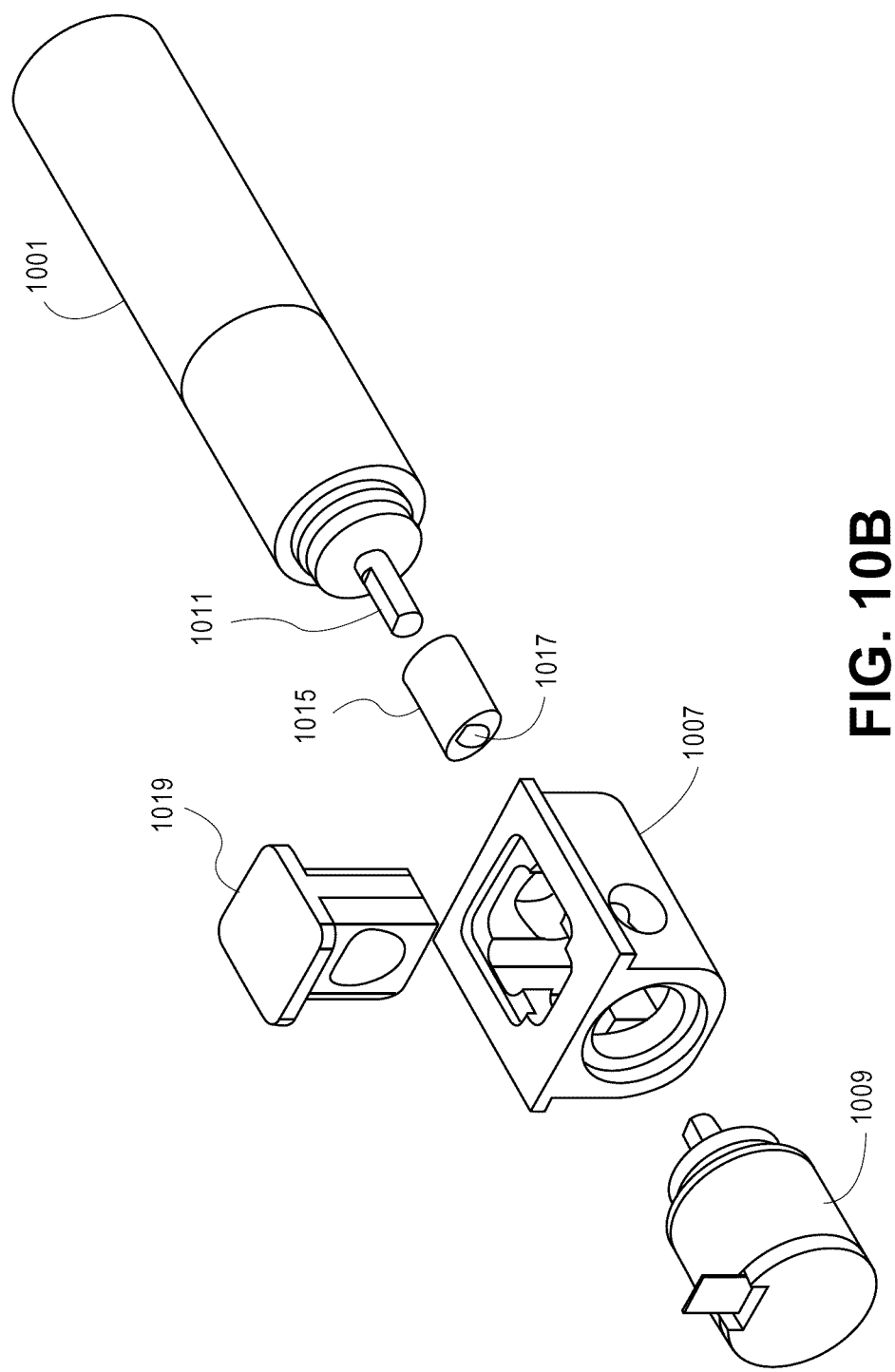

PERSONAL HEALTH DEVICE

REFERENCE TO RELATED APPLICATION

The present application claims priority benefit under 35 U.S.C. §119(e) to U.S. Provisional Patent Application Ser. No. 61/486,689 filed May 16, 2011, titled "Personal Health Device" hereby incorporated in its entirety by reference herein.

FIELD OF THE DISCLOSURE

The present disclosure relates to the field of non-invasive physiological measurements.

BACKGROUND

The standard of care in caregiver environments includes patient monitoring through spectroscopic analysis using, for example, a pulse oximeter. Devices capable of spectroscopic analysis generally include a light source(s) transmitting optical radiation into or reflecting off a measurement site, such as, body tissue carrying pulsing blood. After attenuation by tissue and fluids of the measurement site, a photo-detection device(s) detects the attenuated light and outputs a detector signal(s) responsive to the detected attenuated light. A signal processing device(s) process the detector(s) signal(s) and outputs a measurement indicative of a blood constituent of interest, such as glucose, oxygen, methemoglobin, total hemoglobin, other physiological parameters, or other data or combinations of data useful in determining a state or trend of wellness of a patient.

In noninvasive devices and methods, a sensor is often adapted to position a finger proximate the light source and light detector. For example, noninvasive sensors often include a clothespin-shaped housing that includes a contoured bed conforming generally to the shape of a finger.

SUMMARY

The present disclosure provides solutions for determining physiological information using optical non-invasive processes by using an active pulse system. The system induces an artificial pulse at a frequency distinguishable from the frequency of a human arterial pulse. As a result, information related to both the arterial pulse as well as the artificial pulse is recoverable from the body. The redundant nature of both pieces of information provide additional information useful in determining physiological parameters.

In an embodiment, a sensor is described which facilitates producing and detecting optical radiation attenuated by body tissue. In an embodiment, a motor is detected which drives a piston into a detector assembly. As a result, the detector assembly creates the artificial pulse. In an embodiment, the detector assembly is configured to stay in constant contact with the body tissue.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIGS. 10A and 10B illustrate embodiments of a motor configuration of an active pulse sensor configuration.

DETAILED DESCRIPTION

Figure 1:
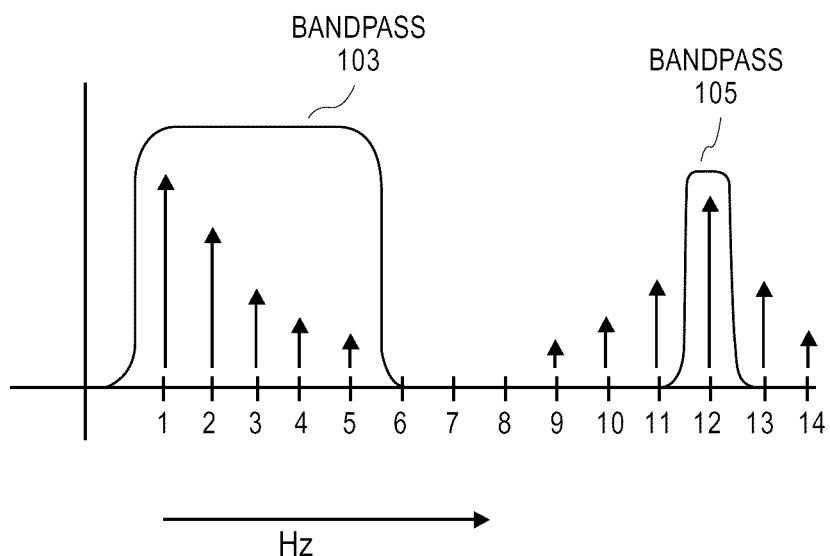
FIG. 1 illustrates a representative frequency display chart.

Reference will now be made to the Figures to discuss embodiments of the present disclosure.

A typical heart beats around 1 Hz creating a fairly predictable heart rate. Determining the heart rate is important for many applications and particularly important for pulse oximetry and noninvasive determination of other parameters using pulse oximetry techniques. This is because the pulse affects light absorption rates at predictable amounts. Thus, knowing the pulse rate is essential to determining accurate non-invasive optical measurements. This information is useful for determining various physiological parameters. These parameters include, for example, a percent value for arterial carbon monoxide saturation ("SpCO"), a percent value for methemoglobin saturation (a brownish-red form of hemoglobin that cannot function as an oxygen carrier) ("SpMet"), fractional $SpO_2$ ("$FpO_2$") or the like. Additionally, caregivers often desire knowledge of $HbO_2$, Hb, carboxyhemoglobin ("HbCO"), methemoglogin ("HbMet"), blood glucose and total hematocrit (Hct), bilirubin, perfusion quality, signal quality or the like Similarly, introducing an artificial excitation can cause perturbations in the blood flow similar to the affects of a heart beat. These artificial excitations can be used as an alternative to the natural pulse rate or in addition to the natural pulse rate. Artificial excitations have the added benefit that the excitations introduced are introduced at known frequencies. Thus, it is not necessary to first determine the pulse rate of an individual. However, it is important to avoid providing artificial excitations at frequencies that over lap with the frequency of the heart rate or its harmonics. In one embodiment, an excitation frequency of five to six times the natural heart rate can be chosen. Moreover, it is also important to provide artificial excitations at frequencies that do not cause discomfort to the patient. Thus, a range of frequencies that are useful for artificial excitations includes a range of about 6 Hz to about 30 Hz. In an embodiment, an excitation in the range of 8 to 15 Hz is chosen. In one embodiment, an artificial excitation is provided at a frequency of about 12 Hz. In one embodiment, an artificial excitation is provided at a frequency of about 8 Hz. Alternatively, the excitation frequency can be chosen to be interspersed with the natural heart frequencies. For example, a frequency of 2.5 Hz can be chosen to avoid harmonics of a 1 Hz heart rate. In an embodiment, the artificial excitation is dynamically chosen based to avoid the heart rate frequencies and harmonics. This can be done by first determining the heart rate and then selecting an artificial excitation frequency once the heart rate is known. In an embodiment, the artificial excitation frequency can be changed during measurements if the heart rate changes. Introducing an artificial excitation generally does not affect the pulse rate or cause any other adverse physical effects on the patient. A typical arterial pulse can cause a pressure change of 2 to 4 psi (100 ml/Hg-200 ml/Hg), while an artificial excitation causes a much lower pressure change.

FIG. 1 is a frequency plot illustrating an embodiment of an active pulse system. As discussed above, a typical heart beats at a frequency around 1 Hz. The pulse typically includes a number of harmonics, usually at 2, 3, 4 and possibly 5 Hz. Thus, a bandpass filter 103 can be selected in order to isolate the expected frequencies of the heart rate. Also illustrated in FIG. 1 is an artificial excitation introduced at 12 Hz. As illustrated the artificial excitation also includes harmonics at 9, 10, 11, 13, 14 and 15 Hz. Because the 12 Hz frequency is known, a narrow bandpass filter 105 can be used to isolate the 12 Hz frequency.

The information from the artificial excitation can then be used to determine either a bulk measurement or venous information. Bulk measurement information can provide a better estimate of mean path length. In order to obtain a bulk measurement, a wavelength of around 1300 nm can be used. Other wavelengths around 1300 nm can also be used. For example, a wavelength of between 1200 nm and 1900 nm can be used. A venous measurement can be obtained by using wavelengths typically associated with standard pulse oximetry measurements, include 660 and 905. In one embodiment, the emitter can emit optical radiation in the form of pulses at wavelengths about 905 nm, about 1050 nm, about 1200 nm, about 1300 nm, about 1330 nm, about 1610 nm, about 1640 nm, and about 1665 nm. In another embodiment, the emitter can emit optical radiation ranging from about 860 nm to about 950 nm, about 950 nm to about 1100 nm, about 1100 nm to about 1270 nm, about 1250 nm to about 1350 nm, about 1300 nm to about 1360 nm, and about 1590 nm to about 1700 nm. Of course, the emitter can transmit any of a variety of wavelengths of visible or near-infrared optical radiation Of course, it will be understood from the disclosure herein that multiple artificial excitations can be introduced at the same time or at different times and at the same or different frequencies in order to obtain both bulk and venous information using the respective wavelengths associated with each measurement.

According to the Beer-Lambert law, light absorption is related to the properties of the materials it passes through as follows:

$$I = I_o e^{-(\mu d)} \quad \text{Eq. 1}$$

The pulse rate and artificial excitations affect different portions of the Eq. 1 as follows:

$$I = I_o e^{-(\mu + \Delta\mu)(d + \Delta d)} \quad \text{Eq. 2}$$

where $\Delta\mu$ is caused by the heart rate and $\Delta d$ is due to the artificial excitation.

Figure 2:
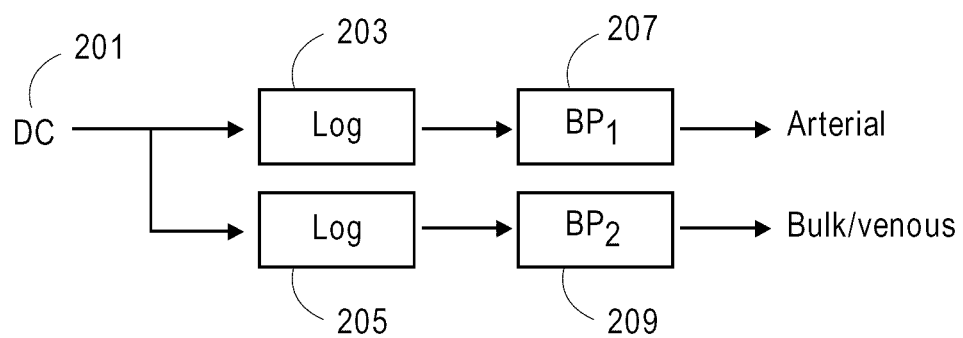
FIG. 2 illustrates a block diagram of a flow of signal processing performed on detected signals.

FIG. 2 illustrates a block diagram for extracting information from the DC portion of the detected light signal. At 201, the DC signal is inputted into the system. The DC signal is then sent along two paths as illustrated. At 203 and 205, the respective DC signals are sent through a log conversion. Log conversions simplify the data so that it is not necessary to know the power of the emitters used. At steps 207 and 209 a bandpass filter is applied to both signals. The bandpass filter in step 207 corresponds to a filter which passes pulse rate frequencies as illustrated in FIG. 1. Similarly, the bandpass filter at step 209 corresponds to the filter which passes the artificial excitation frequency. The output from bandpass 207 is arterial information. The output from 209 is bulk and/or venous information, again depending on the wavelength used.

In an embodiment, the measurements can be continuous or discrete. In an embodiment of a discrete measurement system, or "spot-check" device, three measurements are taken and the two closest measurements are averaged or weighted to determine a displayed measurement. This results in an improved accuracy of 0.1 to 0.2 g/dl in the case of a glucose measurement.

In an embodiment, the metabolic breakdown of glucose is measured over a period time. This can be measured by continuously measuring glucose levels over time and monitoring how glucose levels drop. In an embodiment, the subject being measured is provided with food or drink before the test is started so that the subject has a higher glucose count at the start of the test. The measurement can be displayed as glucose metabolism in g/dl per period of time, such as a minute, ten minutes or per hour.

Figure 2A:
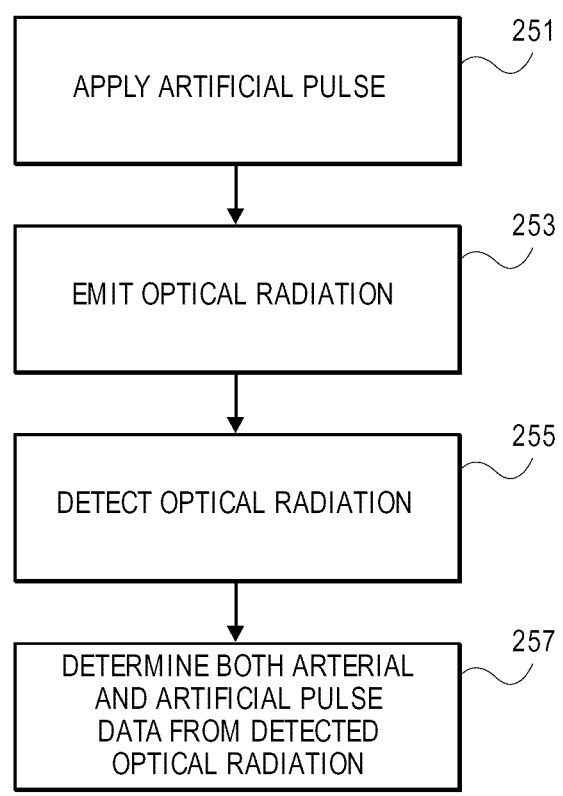
FIG. 2A is a flow diagram of an active pulse measurement system.

FIG. 2A is a flow diagram according to an embodiment of the disclosure. At block 251, an artificial pulse is applied to the measurement site. At block 253, optical radiation is emitted into the measurement site. This can include one or more different wavelengths. At block 255, the emitted optical radiation is detected after attenuation by body tissue which is undergoing an active pulse stimulation. At block 257, the detected optical radiation is used to determine both arterial pulse information and active pulse information. The two different sets of information can then be used to enhance physiological measurement.

Figure 3:
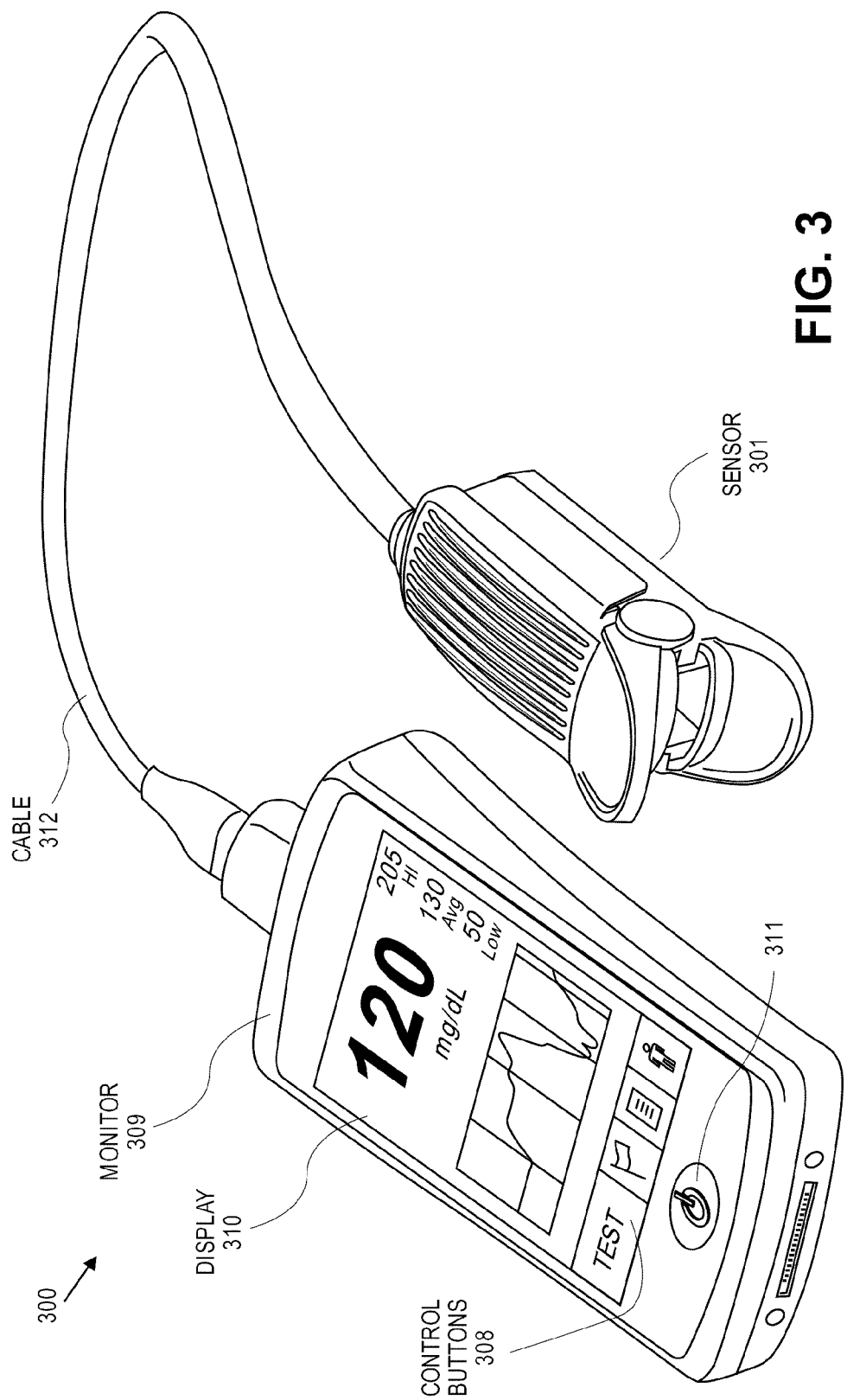
FIG. 3 illustrates an embodiment of a physiological monitor.

FIG. 3 illustrates an example of a monitoring device 300. In the depicted embodiment, the monitoring device 300 includes a finger clip sensor 301 connected to a monitor 309 via a cable 312. In the embodiment shown, the monitor 309 includes a display 310, control buttons 308 and a power button 311. Moreover, the monitor 309 can advantageously include various electronic processing, signal processing, and data storage devices capable of receiving signal data from said sensor 301, processing the signal data to determine one or more output measurement values indicative of one or more physiological parameters of a monitored patient, and displaying the measurement values, trends of the measurement values, combinations of measurement values, and the like.

The cable 312 connecting the sensor 301 and the monitor 309 can be implemented using one or more wires, optical fiber, flex circuits, or the like. In some embodiments, the cable 312 can employ twisted pairs of conductors in order to minimize or reduce cross-talk of data transmitted from the sensor 301 to the monitor 309. Various lengths of the cable 312 can be employed to allow for separation between the sensor 301 and the monitor 309. The cable 312 can be fitted with a connector (male or female) on either end of the cable 312 so that the sensor 301 and the monitor 309 can be connected and disconnected from each other. Alternatively, the sensor 301 and the monitor 309 can be coupled together via a wireless communication link, such as an infrared link, radio frequency channel, or any other wireless communication protocol and channel.

The monitor 309 can be attached to the patient. For example, the monitor 309 can include a belt clip or straps that facilitate attachment to a patient's belt, arm, leg, or the like. The monitor 309 can also include a fitting, slot, magnet, LEMO snap-click connector, or other connecting mechanism to allow the cable 312 and sensor 301 to be attached to the monitor 309.

The monitor 309 can also include other components, such as a speaker, power button, removable storage or memory (e.g., a flash card slot), an AC power port, and one or more network interfaces, such as a universal serial bus interface or an Ethernet port. For example, the monitor 309 can include a display 310 that can indicate a measurement for glucose, for example, in mg/dL. Other analytes and forms of display can also appear on the monitor 309. In an embodiment, the monitor 309 includes an integral or detachable glucose strip reader. A detachable glucose strip reader can be separately housed and configured to communicate wirelessly with monitor 309 or by attachment to a network interface, universal serial bus interface or Ethernet port. In an embodiment, an invasive glucose strip test device can be integrated into the monitor 309. The strip test device can be used as a secondary measure in the case of glucose or in addition to other measurements performed by the monitor 309. In an embodiment, the invasive glucose strip test can be used to calibrate a non-invasive optical glucose measurement. In an embodiment, blood pressure measurements can also be integrated into the monitor 309.

In addition, although a single sensor 301 with a single monitor 309 is shown, different combinations of sensors and device pairings can be implemented. For example, multiple sensors can be provided for a plurality of differing patient types or measurement sites or even patient fingers. In an embodiment, a resposable sensor can be used. A resposable sensor integrates both reusable and disposable components. For example, the emitters, detectors and motor assembly can be reused while the components used to attach the sensor to the patient can be disposable.

Figure 4:
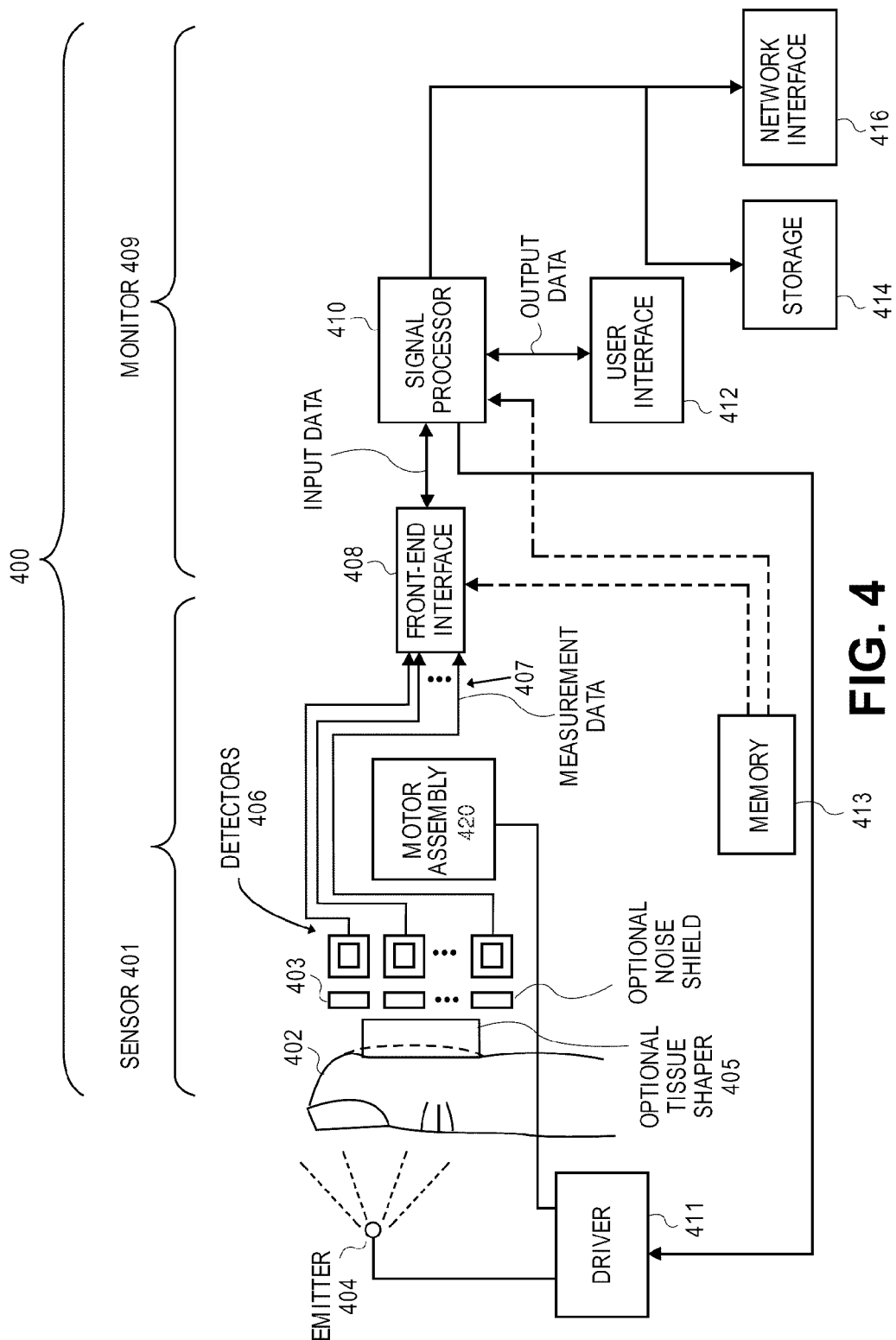
FIG. 4 illustrates a block diagram of a physiological monitor.

FIG. 4 illustrates an example of a data collection system 400. In certain embodiments, the data collection system 400 noninvasively measures a blood analyte, such as oxygen, carbon monoxide, methemoglobin, total hemoglobin, glucose, proteins, glucose, lipids, a percentage thereof (e.g., saturation) or for measuring many other physiologically relevant patient characteristics. The system 400 can also measure additional blood analytes and/or other physiological parameters useful in determining a state or trend of wellness of a patient.

The data collection system 400 can measuring optical radiation from the measurement site. The optical radiation can be used to determine analyte concentrations, including glucose, total hemoglobin, methemoglobin, carboxyhemoglobin, oxygen saturation, etc., at least in part by detecting light attenuated by a measurement site 402. The measurement site 402 can be any location on a patient's body, such as a finger, foot, ear lobe, or the like. For convenience, this disclosure is described primarily in the context of a finger measurement site 402. However, the features of the embodiments disclosed herein can be used with other measurement sites 402.

In the depicted embodiment, the system 400 includes an optional tissue thickness adjuster or tissue shaper 405, which can include one or more protrusions, bumps, lenses, or other suitable tissue-shaping mechanisms. In certain embodiments, the tissue shaper 405 is a flat or substantially flat surface that can be positioned proximate the measurement site 402 and that can apply sufficient pressure to cause the tissue of the measurement site 402 to be flat or substantially flat. In other embodiments, the tissue shaper 405 is a convex or substantially convex surface with respect to the measurement site 402. Many other configurations of the tissue shaper 405 are possible. Advantageously, in certain embodiments, the tissue shaper 405 reduces thickness of the measurement site 402 while preventing or reducing occlusion at the measurement site 402. Reducing thickness of the site can advantageously reduce the amount of attenuation of the light because there is less tissue through which the light must travel. Shaping the tissue into a convex (or alternatively concave) surface can also provide more surface area from which light can be detected.

The embodiment of the data collection system 400 shown also includes an optional noise shield 403. In an embodiment, the noise shield 403 can be advantageously adapted to reduce electromagnetic noise while increasing the transmittance of light from the measurement site 402 to one or more detectors 406 (described below). For example, the noise shield 403 can advantageously include a conductive coated glass or metal grid electrically communicating with one or more other shields of the sensor 401 or electrically grounded. Also included is an active pulse motor 420 (described below).

The data collection system 400 can include a sensor 401 (or multiple sensors) that is coupled to a processing device or physiological monitor 409. In an embodiment, the sensor 401 and the monitor 409 are integrated together into a single unit. In another embodiment, the sensor 401 and the monitor 409 are separate from each other and communicate one with another in any suitable manner, such as via a wired or wireless connection. The sensor 401 and monitor 409 can be attachable and detachable from each other for the convenience of the user or caregiver, for ease of storage, sterility issues, or the like. The sensor 401 and the monitor 409 will now be further described.

In the depicted embodiment shown in FIG. 4, the sensor 401 includes an emitter 404, a tissue shaper 405, a set of detectors 406, and a front-end interface 408. The emitter 404 can serve as the source of optical radiation transmitted towards measurement site 402. As will be described in further detail below, the emitter 404 can include one or more sources of optical radiation, such as LEDs, laser diodes, incandescent bulbs with appropriate frequency-selective filters, combinations of the same, or the like. In an embodiment, the emitter 404 includes sets of optical sources that are capable of emitting visible and near-infrared optical radiation.

In some embodiments, the emitter 404 is used as a point optical source, and thus, the one or more optical sources of the emitter 404 can be located within a close distance to each other, such as within about a 2 mm to about 4 mm. The emitters 404 can be arranged in an array, such as is described in U.S. Publication No. 2006/0211924, filed Sep. 21, 2006, titled "Multiple Wavelength Sensor Emitters," the disclosure of which is hereby incorporated by reference in its entirety. In particular, the emitters 404 can be arranged at least in part as described in paragraphs [0061] through [0068] of the aforementioned publication, which paragraphs are hereby incorporated specifically by reference. Other relative spatial relationships can be used to arrange the emitters 404.

The data collection system 400 also includes a driver 411 that drives the emitter 404. The driver 411 can be a circuit or the like that is controlled by the monitor 409. For example, the driver 411 can provide pulses of current to the emitter 404. In an embodiment, the driver 411 drives the emitter 404 in a progressive fashion, such as in an alternating manner. The driver 411 can drive the emitter 404 with a series of pulses of about 1 milliwatt (mW) for some wavelengths that can penetrate tissue relatively well and from about 40 mW to about 100 mW for other wavelengths that tend to be significantly absorbed in tissue. A wide variety of other driving powers and driving methodologies can be used in various embodiments.

The driver 411 can be synchronized with other parts of the sensor 401 and can minimize or reduce jitter in the timing of pulses of optical radiation emitted from the emitter 404. For example, in an embodiment, the timing of the pulses is synchronized with the timing of the motor 420 revolutions. In some embodiments, the driver 411 is capable of driving the emitter 404 to emit optical radiation in a pattern that varies by less than about 10 parts-per-million.

The detectors 406 capture and measure light from the measurement site 402. For example, the detectors 406 can capture and measure light transmitted from the emitter 404 that has been attenuated or reflected from the tissue in the measurement site 402. The detectors 406 can output a detector signal 407 responsive to the light captured or measured. The detectors 406 can be implemented using one or more photodiodes, phototransistors, or the like.

In addition, the detectors 406 can be arranged with a spatial configuration to provide a variation of path lengths among at least some of the detectors 406. That is, some of the detectors 406 can have the substantially, or from the perspective of the processing algorithm, effectively, the same path length from the emitter 404. However, according to an embodiment, at least some of the detectors 406 can have a different path length from the emitter 404 relative to other of the detectors 406. Variations in path lengths can be helpful in allowing the use of a bulk signal stream from the detectors 406. In some embodiments, the detectors 406 may employ a linear spacing, a logarithmic spacing, or a two or three dimensional matrix of spacing, or any other spacing scheme in order to provide an appropriate variation in path lengths.

Active Pulse Motor 420 rotates providing an agitation at a known frequency which is transferred through the sensor to the measurement site. The motor 420 is driven by driver 411. The vibration created by the motor 420 is useful in determining further information regarding the physiological state of the patient as described in more detail below.

The front end interface 408 provides an interface that adapts the output of the detectors 406, which is responsive to desired physiological parameters. For example, the front end interface 408 can adapt a signal 407 received from one or more of the detectors 406 into a form that can be processed by the monitor 409, for example, by a signal processor 410 in the monitor 409. The front end interface 408 can have its components assembled in the sensor 401, in the monitor 409, in connecting cabling (if used), combinations of the same, or the like. The location of the front end interface 408 can be chosen based on various factors including space desired for components, desired noise reductions or limits, desired heat reductions or limits, and the like.

The front end interface 408 can be coupled to the detectors 406 and to the signal processor 410 using a bus, wire, electrical or optical cable, flex circuit, or some other form of signal connection. The front end interface 408 can also be at least partially integrated with various components, such as the detectors 406. For example, the front end interface 408 can include one or more integrated circuits that are on the same circuit board as the detectors 406. Other configurations can also be used.

The front end interface 408 can be implemented using one or more amplifiers, such as transimpedance amplifiers, that are coupled to one or more analog to digital converters (ADCs) (which can be in the monitor 409), such as a sigma-delta ADC. A transimpedance-based front end interface 408 can employ single-ended circuitry, differential circuitry, and/or a hybrid configuration. A transimpedance-based front end interface 408 can be useful for its sampling rate capability and freedom in modulation/demodulation algorithms. For example, this type of front end interface 408 can advantageously facilitate the sampling of the ADCs being synchronized with the pulses emitted from the emitter 404 and/or vibrations from the motor 420.

The ADC or ADCs can provide one or more outputs into multiple channels of digital information for processing by the signal processor 410 of the monitor 409. Each channel can correspond to a signal output from a detector 406.

In some embodiments, a programmable gain amplifier (PGA) can be used in combination with a transimpedance-based front end interface 408. For example, the output of a transimpedance-based front end interface 408 can be output to a PGA that is coupled with an ADC in the monitor 409. A PGA can be useful in order to provide another level of amplification and control of the stream of signals from the detectors 406. Alternatively, the PGA and ADC components can be integrated with the transimpedance-based front end interface 408 in the sensor 401.

In another embodiment, the front end interface 408 can be implemented using switched-capacitor circuits. A switched-capacitor-based front end interface 408 can be useful for, in certain embodiments, its resistor-free design and analog averaging properties. In addition, a switched-capacitor-based front end interface 408 can be useful because it can provide a digital signal to the signal processor 410 in the monitor 409.

As shown in FIG. 4, the monitor 409 can include the signal processor 410 and a user interface, such as a display 412. The monitor 409 can also include optional outputs alone or in combination with the display 412, such as a storage device 414 and a network interface 416. In an embodiment, the signal processor 410 includes processing logic that determines measurements for desired analytes, such as glucose and total hemoglobin, based on the signals received from the detectors 406. The signal processor 410 can be implemented using one or more microprocessors or subprocessors (e.g., cores), digital signal processors, application specific integrated circuits (ASICs), field programmable gate arrays (FPGAs), combinations of the same, and the like.

The signal processor 410 can provide various signals that control the operation of the sensor 401. For example, the signal processor 410 can provide an emitter control signal to the driver 411. This control signal can be useful in order to synchronize, minimize, or reduce jitter in the timing of pulses emitted from the emitter 404 or motor vibrations from motor 420. Accordingly, this control signal can be useful in order to cause optical radiation pulses emitted from the emitter 404 to follow a precise timing and consistent pattern. For example, when a transimpedance-based front end interface 408 is used, the control signal from the signal processor 410 can provide synchronization with the ADC in order to avoid aliasing, cross-talk, and the like. As also shown, an optional memory 413 can be included in the front-end interface 408 and/or in the signal processor 410. This memory 413 can serve as a buffer or storage location for the front-end interface 408 and/or the signal processor 410, among other uses.

The user interface 412 can provide an output, e.g., on a display, for presentation to a user of the data collection system 400. The user interface 412 can be implemented as a touch-screen display, an LCD display, an organic LED display, or the like. In addition, the user interface 412 can be manipulated to allow for measurement on the non-dominant side of the patient. For example, the user interface 412 can include a flip screen, a screen that can be moved from one side to another on the monitor 409, or can include an ability to reorient its display indicia responsive to user input or device orientation. In alternative embodiments, the data collection system 400 can be provided without a user interface 412 and can simply provide an output signal to a separate display or system.

A storage device 414 and a network interface 416 represent other optional output connections that can be included in the monitor 409. The storage device 414 can include any computer-readable medium, such as a memory device, hard disk storage, EEPROM, flash drive, or the like. The various software and/or firmware applications can be stored in the storage device 414, which can be executed by the signal processor 410 or another processor of the monitor 409. The network interface 416 can be a serial bus port (RS-232/RS-485), a Universal Serial Bus (USB) port, an Ethernet port, a wireless interface (e.g., WiFi such as any 802.1x interface, including an internal wireless card), or other suitable communication device(s) that allows the monitor 409 to communicate and share data with other devices. The monitor 409 can also include various other components not shown, such as a microprocessor, graphics processor, or controller to output the user interface 412, to control data communications, to compute data trending, or to perform other operations. In an embodiment, the measurements are encrypted and decrypted inside the processor in hardware. As a result, the measurements can be safely stored and communicated to, for example, a cloud based storage medium without compromising the security of the data.

Although not shown in the depicted embodiment, the data collection system 400 can include various other components or can be configured in different ways. For example, the sensor 401 can have both the emitter 404 and detectors 406 on the same side of the measurement site 402 and use reflectance to measure analytes. The data collection system 400 can also include a sensor that measures the power of light emitted from the emitter 404.

Figure 5:
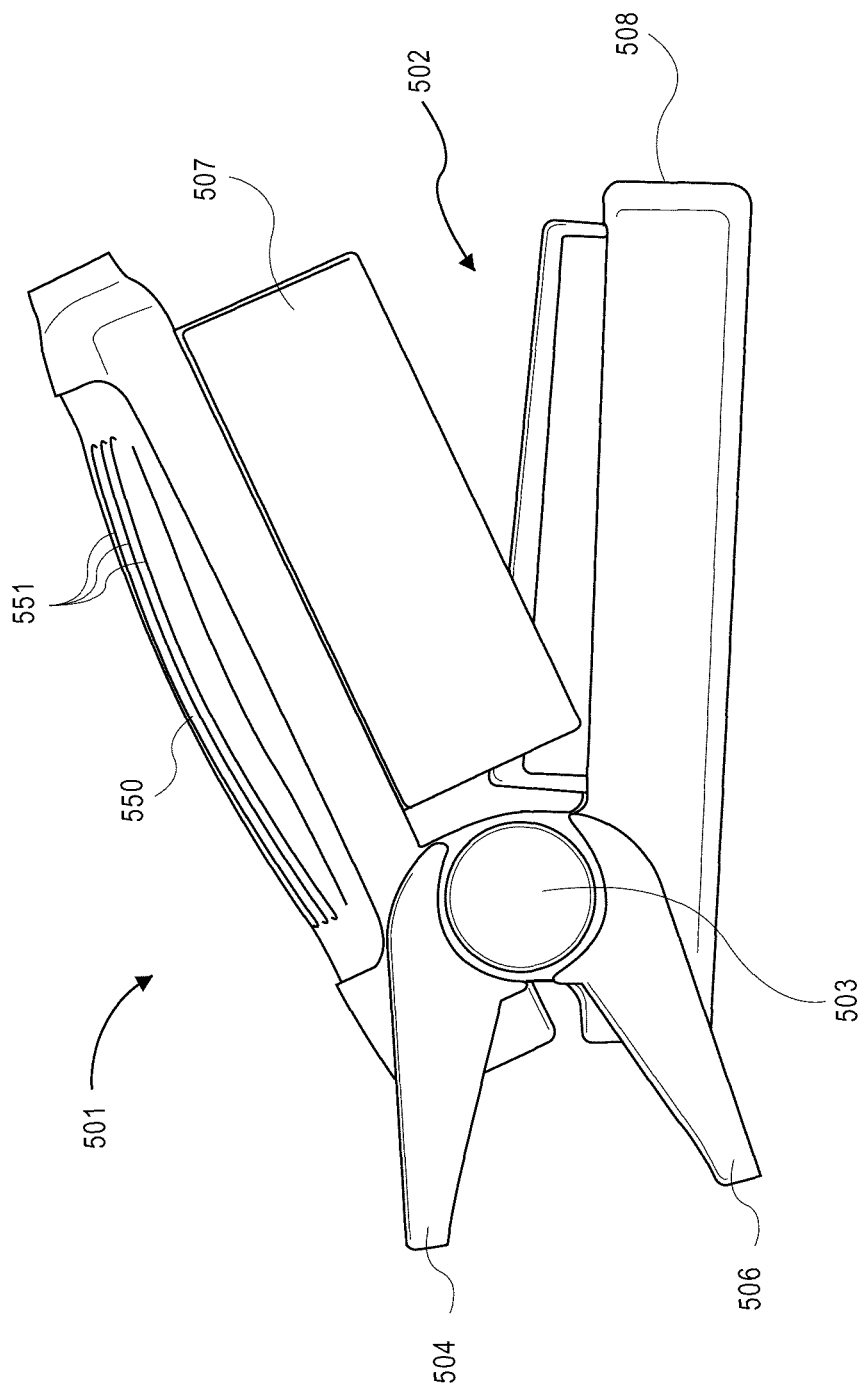
FIG. 5 illustrates a side view of a physiological sensor.

FIGS. 5-10 illustrate more detailed examples of embodiments of the sensor 301. Referring to FIG. 5, the sensor 501 in the depicted embodiment is a clothespin-shaped clip sensor that includes an enclosure 502 for receiving a patient's finger. The enclosure 502 is formed by an upper section or emitter shell 504, which is pivotably connected with a lower section or detector shell 506. The emitter shell 504 can be biased with the detector shell 506 to close together around a pivot point 503 and thereby sandwich finger tissue between the emitter and detector shells 504, 506.

In an embodiment, the pivot point 503 advantageously includes a pivot capable of adjusting the relationship between the emitter and detector shells 504, 506 to effectively level the sections when applied to a tissue site. In another embodiment, the sensor 501 includes some or all features of the finger clip described in U.S. Publication No. 2006/0211924, incorporated above, such as a spring that causes finger clip forces to be distributed along the finger. Paragraphs [0096] through [0105], which describe this feature, are hereby specifically incorporated by reference.

The emitter shell 50a can position and house various emitter components of the sensor 501. It can be constructed of reflective material (e.g., white silicone or plastic) and/or can be metallic or include metalicized plastic (e.g., including carbon and aluminum) to possibly serve as a heat sink. The emitter shell 504 can also include absorbing opaque material, such as, for example, black or grey colored material, at various areas, such as on one or more flaps 507, to reduce ambient light entering the sensor 501.

The detector shell 506 can position and house one or more detector portions of the sensor 501. The detector shell 506 can be constructed of reflective material, such as white silicone or plastic. As noted, such materials can increase the usable signal at a detector by forcing light back into the tissue and measurement site (see FIG. 1). The detector shell 506 can also include absorbing opaque material at various areas, such as lower area 508, to reduce ambient light entering the sensor 501.

Figure 6:
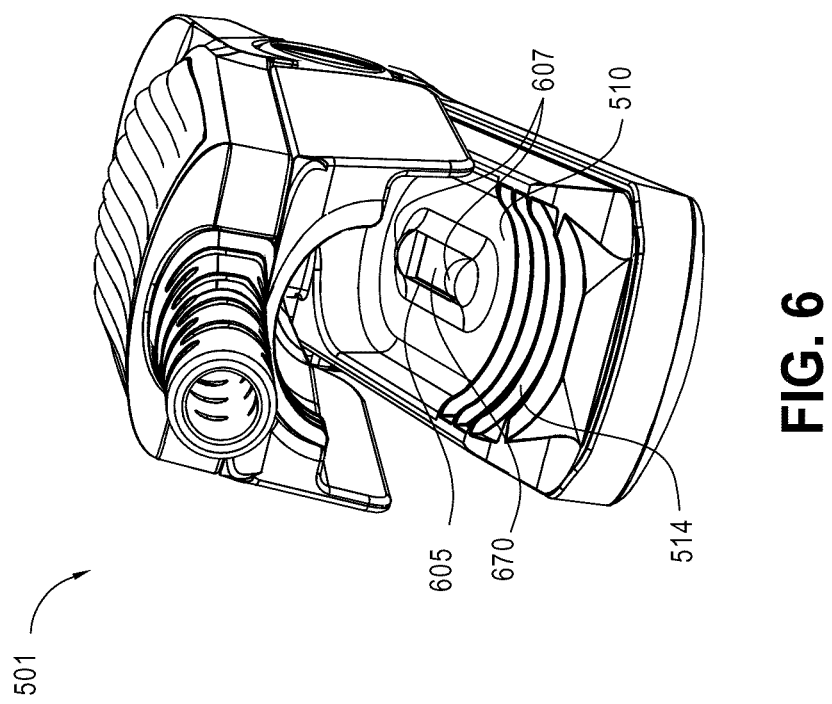
FIG. 6 illustrates a perspective view of a physiological sensor.

FIG. 6 illustrates another view of the sensor 301, which includes an embodiment of a partially cylindrical protrusion 605. The finger bed 510 includes a generally curved surface shaped generally to receive tissue, such as a human digit. The finger bed 510 also includes the ridges or channels 514. The finger bed 310 shown also includes the protrusion 605.

Figure 7:
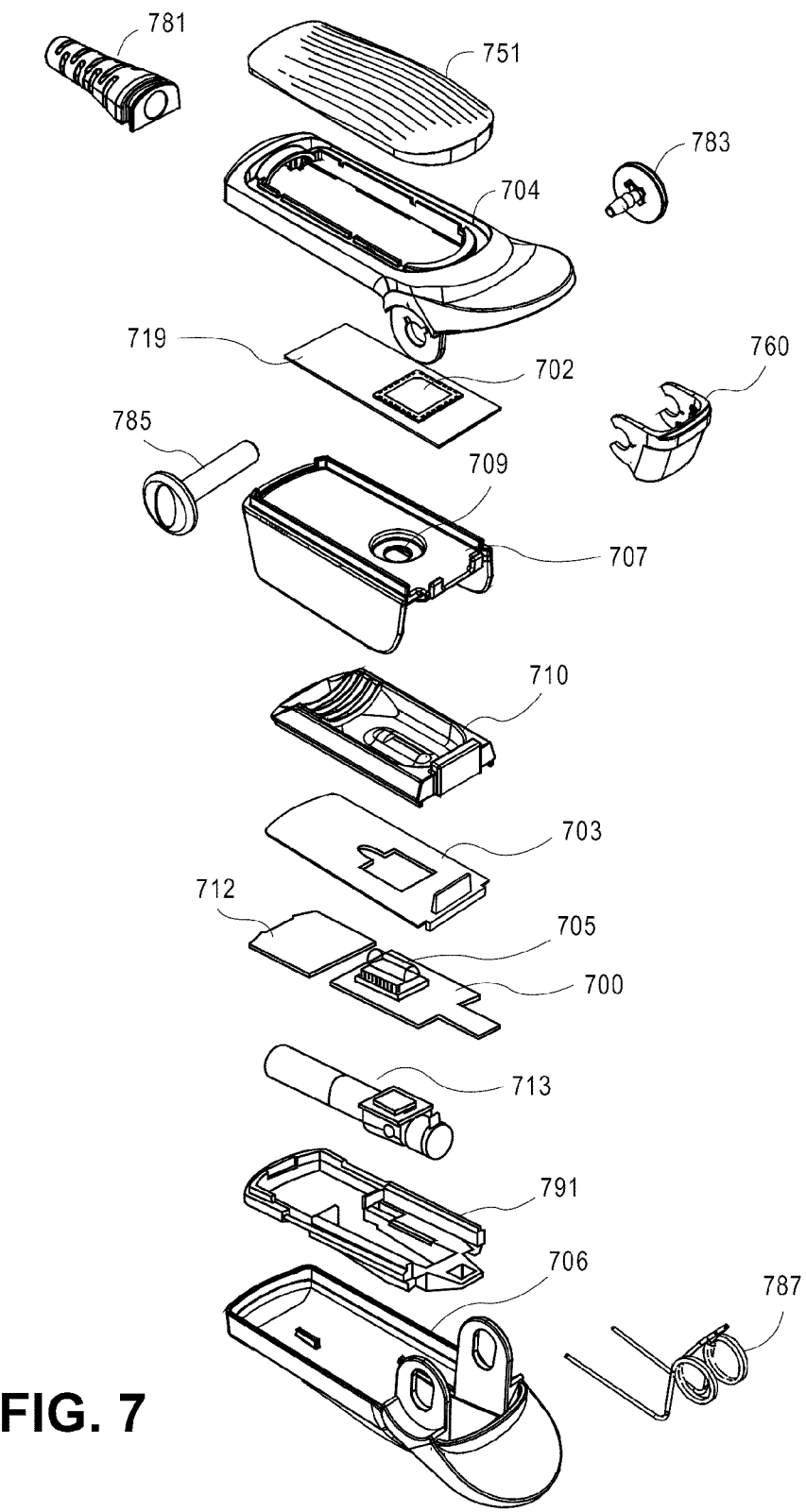
FIG. 7 illustrates an exploded view of a physiological sensor.

FIG. 7 illustrates an exploded view of certain of the components of the sensor 301 described above. A heat sink 751 and a cable 781 attach to an emitter shell 704. The emitter shell attaches to a flap housing 707 attached to an emitter submount 702, which is attached to a circuit board 719. flap housing 707 includes emitter window 709.

A spring 787 attaches to a detector shell 706 via pins 783, 785, which hold the emitter and detector shells 704, 706 together. A support structure 791 attaches to the detector shell 706. A motor assembly 713 attaches to the support structure 791 and presses against the detector submount 700. In an embodiment, submount 700 is floating, in other words, it is not fixedly attached but is allowed to float within the surrounding support structures. This allows the submount 700 to move freely when pressed by the motor assembly 713. Submount 712 attaches to support structure 791. A finger bed 710 provides a surface for placement of the patient's finger. Finger bed 710 can comprise a gripping surface or gripping features, which can assist in placing and stabilizing a patient's finger in the sensor. A partially cylindrical protrusion 705 can also be disposed in the finger bed 710. As shown, finger bed 710 attaches to the noise shield 703. The noise shield 703 may be configured to reduce noise, such as from ambient light and electromagnetic noise. For example, the noise shield 703 may be constructed from materials having an opaque color, such as black or a dark blue, to prevent light piping.

Noise shield 703 may also comprise a thermistor. The thermistor can be helpful in measuring the temperature of a patient's finger. For example, the thermistor may be useful in detecting when the patient's finger is reaching an unsafe temperature that is too hot or too cold. In addition, the temperature of the patient's finger may be useful in indicating to the sensor the presence of low perfusion as the temperature drops. In addition, the thermistor may be useful in detecting a shift in the characteristics of the water spectrum in the patient's finger, which can be temperature dependent.

A flex circuit cover 760 attaches to the pins 783, 785. A flex circuit can also be provided that connects the circuit board 719 with the submount 700 (or a circuit board to which the submount 700 is connected). A flex circuit protector 760 may be provided to provide a barrier or shield to the flex circuit. In particular, the flex circuit protector 760 may also prevent any electrostatic discharge to or from the flex circuit. The flex circuit protector 760 may be constructed from well known materials, such as a plastic or rubber materials.

Figure 8:
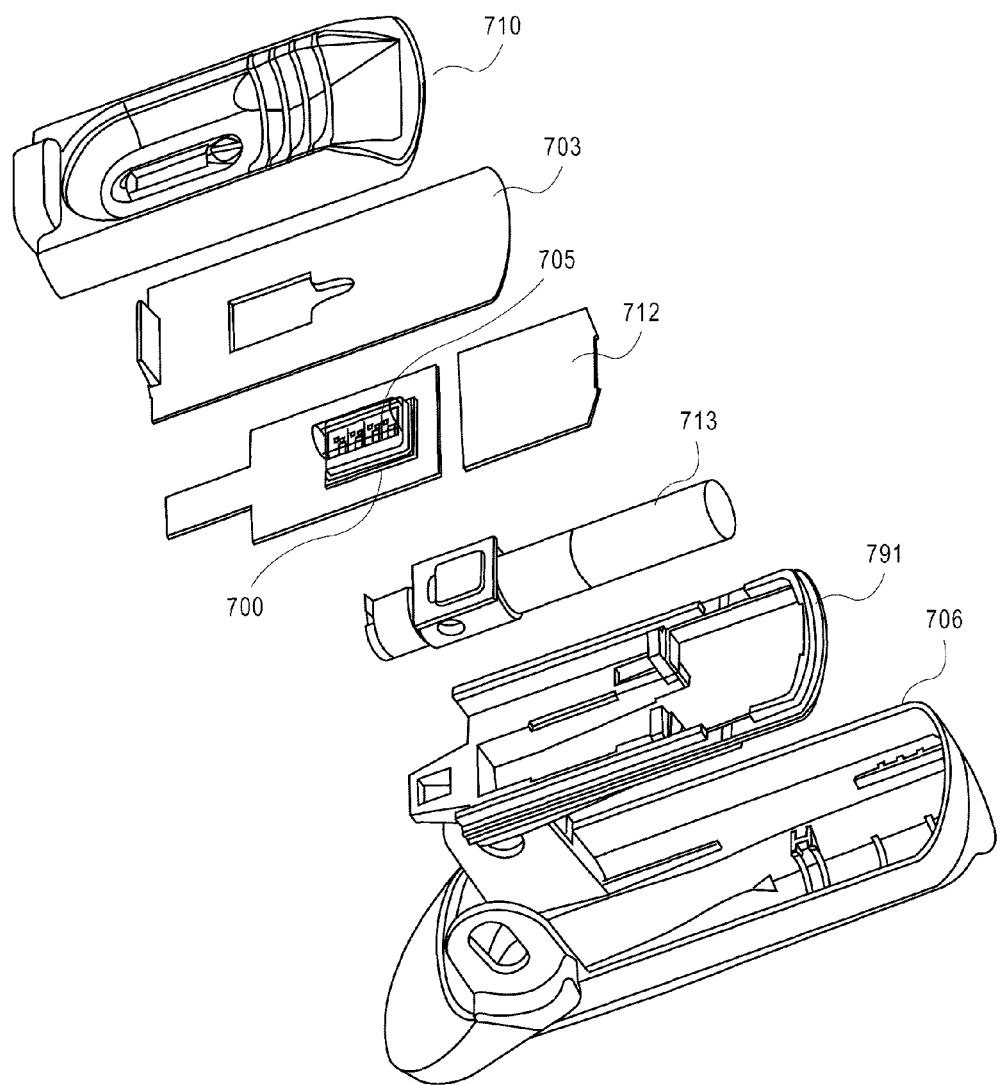
FIGS. 8 and 9 illustrate different perspectives of an exploded view of an active pulse configuration of a portion of a physiological sensor.
Figure 9:
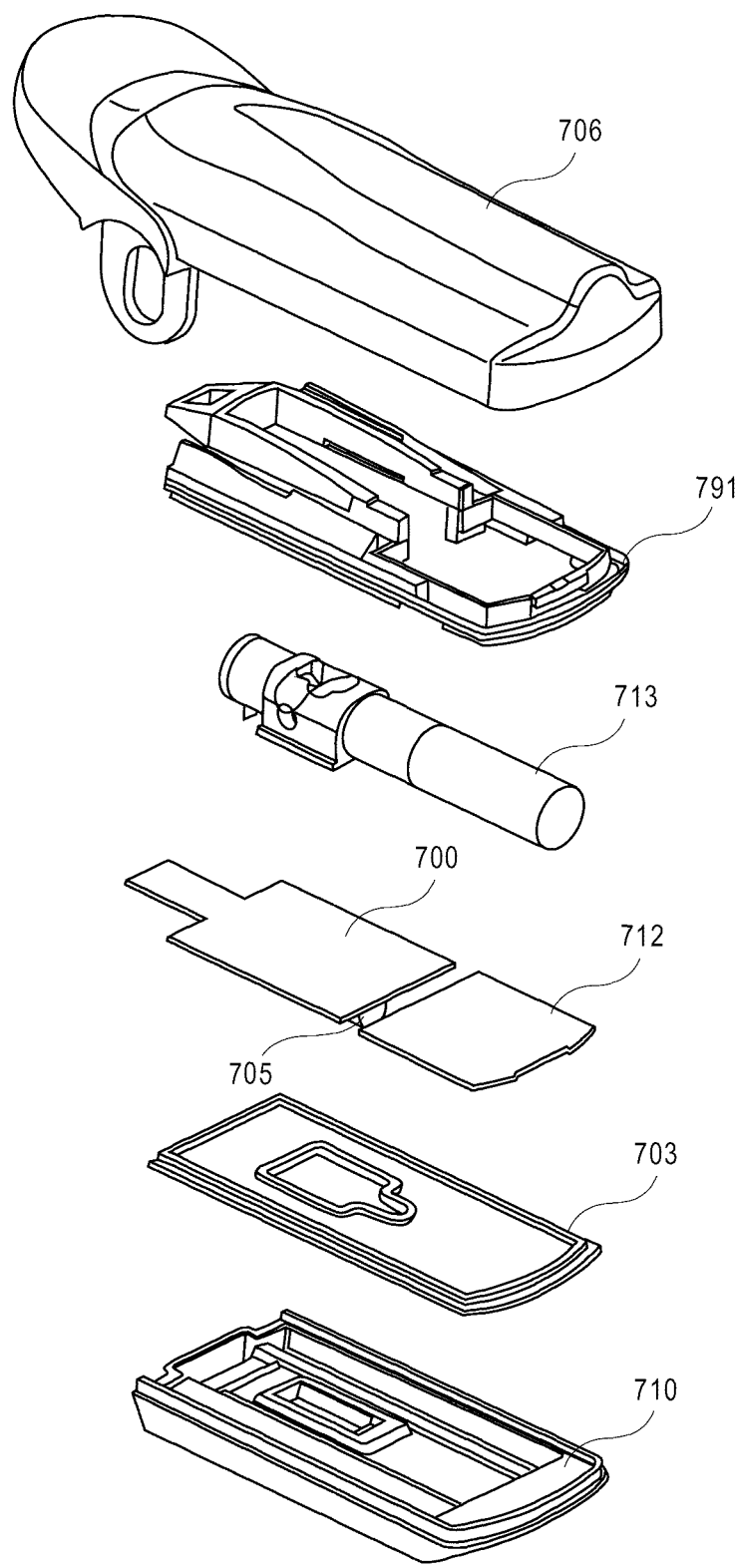

FIGS. 8 and 9 illustrate different perspective views of some of the components of FIG. 7.

Figure 10A:
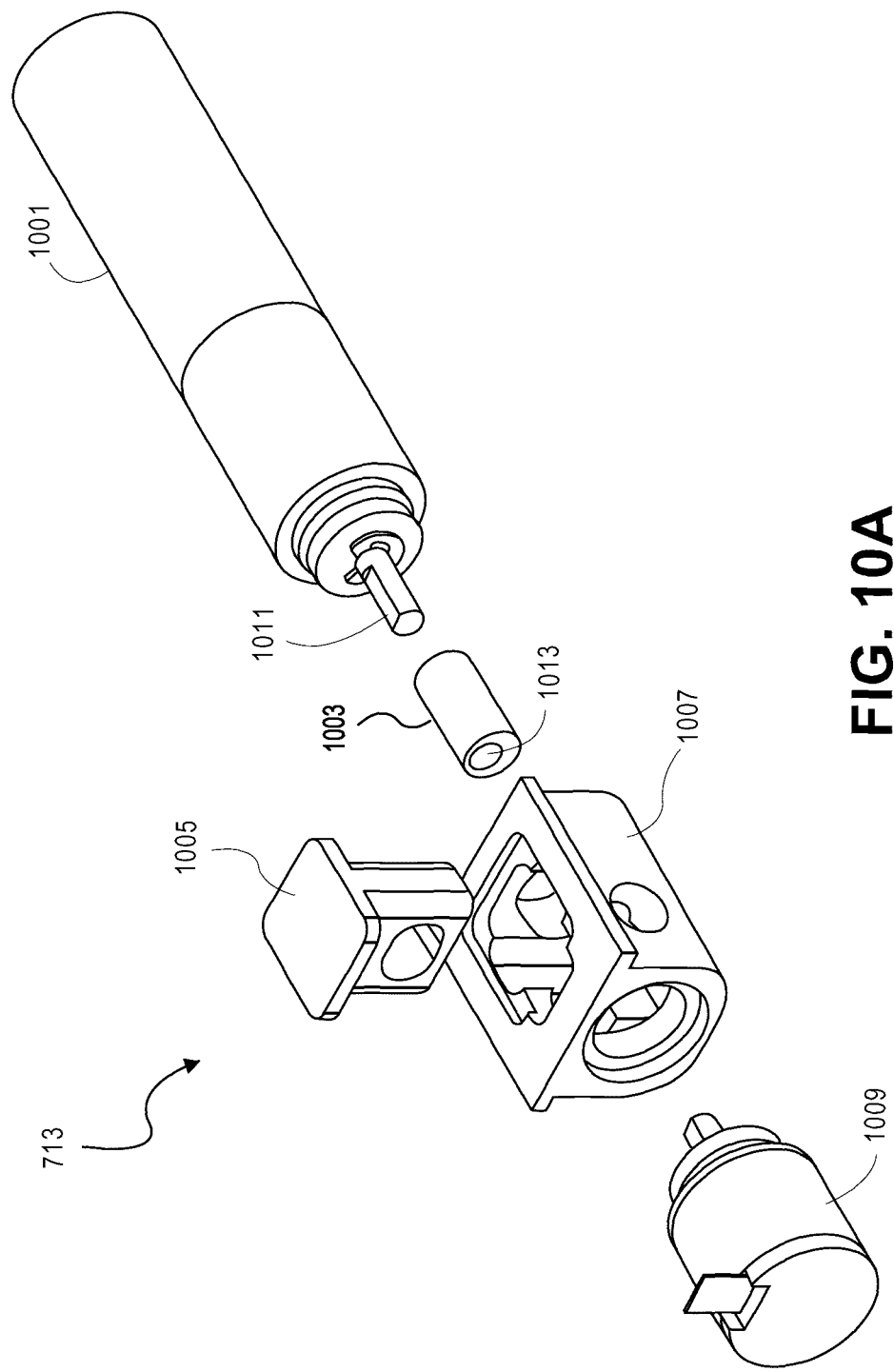

FIG. 10A is an exploded view of the motor assembly 713. The motor assembly 713 includes a motor 1001, actuator 1003, actuator housing 1007, piston 1005 and servo controller 1009. The motor 1001 rotates an axle 1011 upon application of an electric current. The axle 1011 is coupled to shaft 1013 of actuator 1003. The shaft 1013 is configured to be off-balance or decentralized. The actuator 1003 is placed inside the actuator housing 1007 along with piston 1005. Servo controller 1009 is also included in the actuator housing 1007 as illustrated. The servo controller monitors the rotation of the motor 1001 and provides feedback to the driver 411. Based on the feedback from the servo controller 1009, the driver 411 adjusts power to the motor 1001 to achieve a desired rotations speed. An important aspect of the motor is the ability to tightly control the speed of the motor in order to achieve and accurate desired frequency of rotation. As depicted, the motor 1001 is a DC motor that is controlled using a servo encoder. In an alternative embodiment, a brushless or step-motor is used.

In operation, the motor 1001 spins the axle 1011. The axle 1011 rotates the actuator 1003. Due to the off-balance nature of the actuator 1003, the actuator will spin unevenly. This uneven rotation moves the piston 1005 up and down, perpendicular to the rotational axis of the motor 1011. The piston 1005 then pushes against submount 700 which pushes cylindrical protrusion 705 into the patient's tissue causing an artificial vibration at a known frequency.

Importantly, protrusion 705 maintains contact with the patient's tissue. As a result, the detector(s) 406 are kept at the same distance relative to the patient's tissue throughout the operation of the artificial vibration. This prevents optical errors from being introduced into the system. The force provided to the piston 1005 should be sufficiently high to affect the perfusion of the tissue site while not exceeding mechanical or patient comfort constraints. In an embodiment, the piston is driven with a force that drives the protrusion 705 about 0.3 mm into the tissue site. In an embodiment, sufficient force is provided to drive the protrusion 705 between about 0.1 mm and about 0.5 mm into the tissue site. In an embodiment, the pressure required to drive the protrusion 705 into the tissue site is between about 80 g and 120 g. In an embodiment, the pressure required to drive the protrusion 705 into the tissue site is about 5 g to about 20 g of pressure higher than the pressure applied by the spring clip of the sensor 501.

FIG. 10B illustrates another embodiment of a motor assembly 713. In the embodiment shown in FIG. 10B, the actuator 1015 has a generally oval cylindrical shape with shaft 1017. The oval shape allows the motor assembly to produce two times the active pulses per revolution as actuator 1003. The oval shape also provides a different shape to the pulse wave than actuator 1003. Piston 1019 is also shaped to be driven by actuator 1015.

In an embodiment, the personal health device disclosed herein is packaged with instructions for using the personal health device. In an embodiment, the instructions are purely graphical in nature so as to be universally understood by all users independent of reading capabilities or language skills.

Phase Shift Effects

Applying an artificial pulse or excitation can induce a phase shift in measurements among wavelengths used. Each wavelength probes the finger in different regions depending on scattering. Wavelengths with lower scattering probe the finger in a straight path from source to detector. Wavelengths with higher scattering probe the finger in a curved and broader path. Because the arterial pressure wave has a delay when it travels through the arteries and capillaries, the wavelengths with lower scattering are modulated by a pressure wave that travels closer to the finger's center and therefore has a smaller delay. The wavelengths with higher scattering are modulated by pressure waves that cover a broader area in the finger and therefore have a larger delay. The result is a measureable shift in time among wavelengths depending on the scattering values, absorption and finger/sensor geometry. This measurable shift can be used to estimate scattering properties and finger geometry which will remove errors observed from one finger to another. For example, in an embodiment, measureable phase shifts can be compared to empirically obtained data based on a cross section of the population. The comparison can then be used to compensate for error observed in the empirical data.

Figure 11:
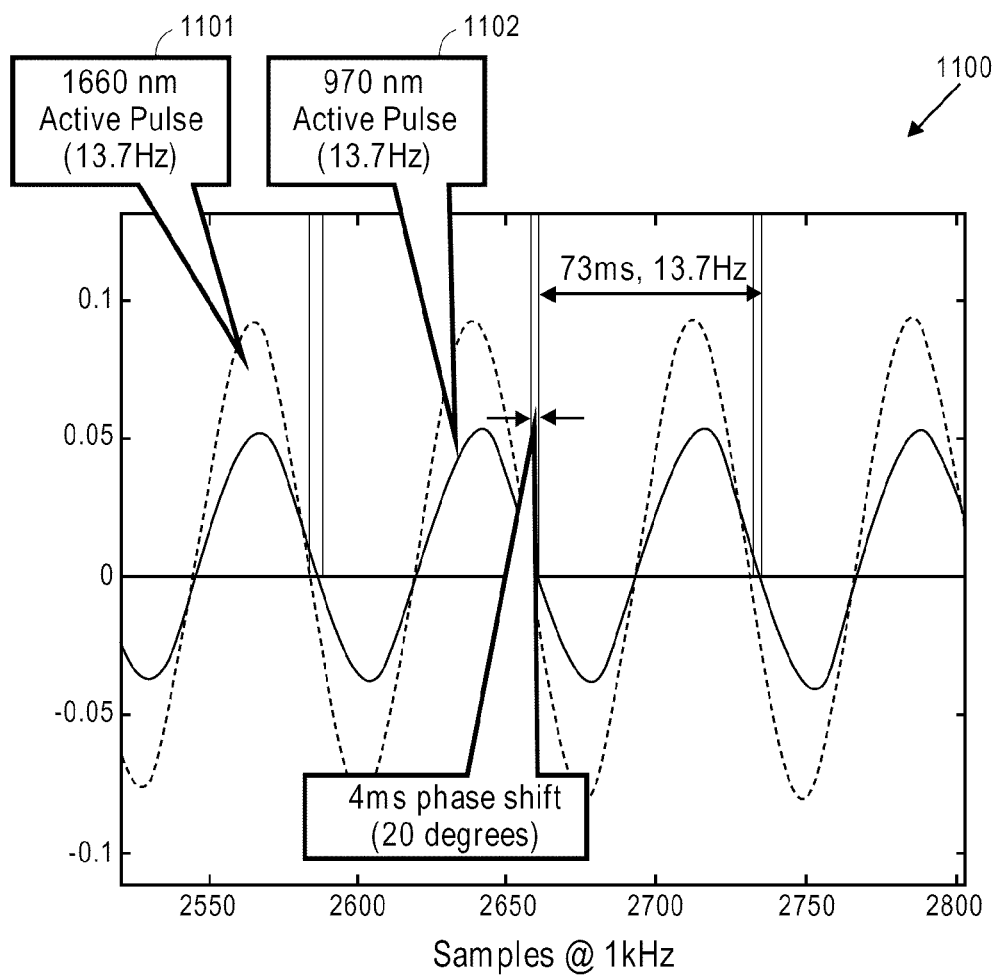
FIG. 11 illustrates an example of phase shift among wavelengths.

FIG. 11 illustrates an example of phase shift. In the example of FIG. 11, graph 1100 illustrates a phase plot of two wavelengths when an active pulse of 13.7 Hz is applied to the measurement site. Wavelength 1660 nm (1101) has an observed phase shift of 20 degrees or 4 ms with respect to wavelength 970 nm (1102).

Figure 12:
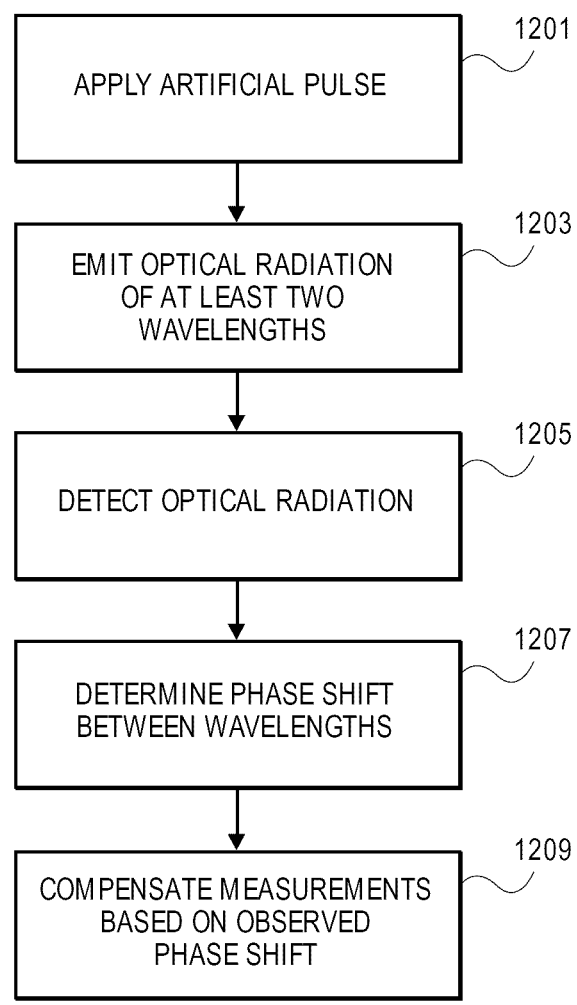
FIG. 12 is a flow diagram of a phase shift measurement system.

FIG. 12 is a flow diagram of a phase shift measurement process. At block 1201, an artificial pulse is applied to the measurement site. At 1203, optical radiation of at least two different wavelengths is projected into the measurement site. At 1205, the optical radiation is detected after attenuation by the tissue undergoing the active pulse stimulation. At block 1207, a phase shift is determined between the wavelengths. At block 1209, the phase shift determination is used to compensate measurement data.

Terminology/Additional Embodiments

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A system configured to determine one or more physiological parameters noninvasively using optical based techniques, the system comprising:
    one or more light emitting devices configured to emit light at one or more wavelengths into a measurement site of a patient;
    one or more detectors configured to detect light emitted from the one or more light emitting devices after absorption by body tissue, and generate a detector signal, the one or more detectors comprising a submount configured to actuate relative to a support structure of the one or more detectors, the submount comprising a protrusion having a cylindrical shape;
    at least one motor configured to rotate at a known rate providing an agitation through the submount and the protrusion at a known frequency at the measurement site to generate a pulse wave which is transferred to the body tissue, the pulse wave generated at a frequency higher than at least two harmonics of a natural heart rate of the patient and lower than about 50 Hz, the motor comprising an actuator of an oval cylindrical shape including a shaft, wherein the motor is configured to actuate the submount with a force that drives that protrusion between about 0.1 mm and about 0.5 mm into the measurement site and wherein the protrusion maintains in contact with the measurement site during measurement;
    a processor configured to receive the detector signal, wherein the detector signal is indicative of the natural heart rate pulse of the patient and the generated pulse wave, the processor configured to determine at least one physiological parameter of the body tissue under measurement by compensating the detected information indicative of the natural heart rate pulse with information indicative of the generated pulse wave; and
    a user interface configured to receive and display the at least one physiological parameter of the body tissue under measurement determined by the processor.

2. The system of claim 1, wherein the generated pulse wave does not affect the arterial pulse wave.

3. The system of claim 1, wherein a change in pressure in the body tissue caused by the generated pulse wave does not affect the natural heart rate pulse.

4. The system of claim 3, wherein the change in pressure caused by the natural heart rate pulse does not affect the generated pulse wave.

5. The system of claim 1, wherein the generated pulse wave has a frequency between 8 Hz and 12 Hz.

6. The system of claim 5, wherein the generated pulse wave has a frequency of 8 Hz.

7. The system of claim 5, wherein the generated pulse wave has a frequency of 12 Hz.

8. The system of claim 1, wherein the information from the generated pulse wave comprises phase shift information.

9. A method of determining one or more physiological parameters noninvasively using optical based techniques, the method comprising:
    emitting one or more wavelengths of light into a measurement site of a patient using one or more light emitting devices;
    generating a pulse wave, using a motor comprising an actuator of an oval cylindrical shape including a shaft, at the measurement site at a known rate, the pulse wave generated at a frequency higher than at least two harmonics of a natural heart rate of the patient and lower than about 50 Hz;
    detecting the light after attenuation by tissue at the measurement site of the patient using one or more detectors, and generating a signal based on the detected light, wherein the generated signal includes information from both the natural heart rate pulse and the generated pulse;
    driving, using the motor, a submount including a protrusion between about 0.1 mm and about 0.5 mm into the measurement site based on the generated pulse wave, wherein the motor maintains the protrusion in contact with the measurement site; and
    determining and displaying at least one physiological parameter of the patient by compensating the information from the detected natural heart rate pulse with information from the detected generated pulse wave.

10. The method of claim 9, wherein the generated pulse wave does not affect the arterial pulse wave.

11. The method of claim 9, wherein a change in pressure at the measurement site caused by the generated pulse wave does not affect the natural heart rate pulse.

12. The method of claim 11, wherein the change in pressure caused by the natural heart rate pulse does not affect the generated pulse wave.

13. The method of claim 9, wherein the generated pulse wave has a frequency between 8 Hz and 12 Hz.

14. The method of claim 13, wherein the generated pulse wave has a frequency of 8 Hz.

15. The method of claim 13, wherein the generated pulse wave has a frequency of 12 Hz.

16. The method of claim 9, wherein the information from the generated pulse wave comprises phase shift information.

* * * * *